United States Patent [19]  [11] 3,969,303
Prosen  [45] July 13, 1976

[54] LINING MATERIAL FOR ACRYLIC DENTURES AND METHOD OF PREPARING THE SAME

[75] Inventor: Emil M. Prosen, Bala-Cynwyd, Pa.

[73] Assignee: Neoloy Products, Inc., Posen, Ill.

[22] Filed: Aug. 28, 1974

[21] Appl. No.: 501,148

Related U.S. Application Data

[63] Continuation-in-part of Ser. No. 203,423, Nov. 30, 1971, abandoned.

[52] U.S. Cl. ................ 260/31.8 C; 32/2; 260/885; 260/DIG. 36
[51] Int. Cl.² ............ A61C 13/22; C08K 5/12; C08L 31/02
[58] Field of Search ....... 260/31.6, 31.8 C, DIG. 36, 260/885; 106/35; 32/2

[56] References Cited
UNITED STATES PATENTS

| | | | |
|---|---|---|---|
| 2,496,387 | 2/1950 | Fink | 260/DIG. 36 |
| 2,497,451 | 2/1950 | Haefeli | 260/DIG. 36 |
| 2,558,139 | 6/1951 | Knock et al. | 260/DIG. 36 |

*Primary Examiner*—Allan Lieberman
*Attorney, Agent, or Firm*—Cooper, Dunham, Clark, Griffin & Moran

[57] ABSTRACT

The present invention provides a lining material for a polymerized methylmethacrylate denture restoration which consists essentially of an admixture of approximately 40% of methylmethacrylate polymer, approximately 10% of methylmethacrylate monomer, and approximately 50% of butyl phthalyl butyl glycolate. The denture liner material is semi-cured for approximately 5 minutes at a temperature of about 160°F. into a soft, tacky material having no inherent rigidity and which can be manually shaped to conform to an irregular object. The denture liner material can also be semi-cured for approximately 15 minutes at a temperature of 160°F. into a somewhat hard material which is capable of being softened by application of heat and pressure. Both the soft semi-cured liner material and the somewhat hard semi-cured liner material are capable of being finally cured with a polymerized methylmethacrylate denture and adhered thereto to provide a soft liner therefor. The invention also provides methods for preparing the liner material and for adhering it to a polymerized methylmethacrylate denture.

3 Claims, No Drawings

LINING MATERIAL FOR ACRYLIC DENTURES AND METHOD OF PREPARING THE SAME

This application is a continuation-in-part of my co-pending application Ser. No. 203,423 filed Nov. 30, 1971, now abandoned.

The present invention relates to an improved lining material for dentures, and to a method of preparing such lining material for dentures.

One of the preferred synthetic materials for artificial dentures is polymerized methylmethacrylate which is usually prepared by an admixture of a monomer and a polymer of methylmethacrylate to produce the finished denture into which prefabricated teeth are embedded.

Polymerized methylmethacrylate which forms the denture, aside from the embedded teeth, is a somewhat rigid material and during mastication of food occasionally gives rise to gum irritations. Often it is necessary to relieve some spots or portions of the denture to eliminate such irritation because of the denture's inherent rigidity.

It is also understood in the art that after a denture has been used by a patient for a period of time the jaw ridge structure changes and the denture requires alterations in order to accommodate to the changed structure of the jaw ridge. The changes in jaw ridge structure frequently give rise to spaces between the denture and the jaw ridge, and also give rise to spaces between the high points of the jaw ridge of the patient's mouth.

It is also well known in the art that after extraction of natural teeth the jaw structure is caused to swell and that a certain period of time is required for healing of the jaw ridge. If the denture is made immediately after extraction, while the ridges are thick and swollen and have not completely receded, spaces are created between the denture and the ridges when the latter recede.

According to the present invention it has been found that a plastic liner may be provided for polymerized methylmethacrylate dentures which eliminates irritations to the gum and other tissue, and which also accommodates to other irregularities in the patient's mouth which are normally not detectable during impression taking, denture fabrication, and denture rehabilitation work. Also, the present invention provides a liner material which may be applied to a polymerized methylmethacrylate denture to accommodate to the changes in the jaw ridge structure which occur after a period of use; to provide supplemental denture structure after the swollen gums have receded; and to provide supplemental denture material to fill in spaces between the high points of the jaw ridge.

More particularly the present invention provides a liner material for polymerized methylmethacrylate dentures which consists essentially of equal parts of acrylic and a plasticizer, — the acrylic consisting of approximately 40% of finely powdered methylmethacrylate polymer and 10% of methylmethacrylate monomer; and a plasticizer consisting of butyl phthalyl butyl glycolate. The resulting composition of the liner material is approximately 40% methylmethacrylate polymer, 10% methylmethacrylate monomer and 50% butyl phthalyl butyl glycolate.

The butyl phthalyl butyl glycolate plasticizer which is utilized in the preparation of the liner material of the present invention is offered for sale by the Monsanto Company under the trademark SANTICIZER B-16.

It has heretofore been proposed to provide denture lining materials utilizing other plasticizers than the plasticizer of the present invention. Some of the lining materials have been found to have disadvantages in that the plasticizer leaches out when exposed to water at room temperature, — the plasticizer actually dissolving or going into solution with the water, with the result that when the water is removed, the liner material loses as much as 11% of its total weight.

After considerable experimentation I have found that the ideal liner material for polymerized methylmethacrylate dentures consists of approximately 40% by weight of methylmethacrylate polymer, 10% by weight of methylmethacrylate monomer, and 50% by weight of butyl phthalyl butyl glycolate. In arriving at these percentages I have found that the final product is much tackier than other liner materials; that the monomer promotes the solubility of the polymer; that it is much easier to compound the liner material; and that for all practical purposes bubbling during the mixing process is eliminated.

In preparing the liner material of the present invention I have found that the admixture of 40% methylmethacrylate polymer, 10% methylmethacrylate monomer and 50% of butyl phthalyl butyl glycolate should be allowed to stand for about 24 hours without heating. This appears to give a more thorough plasticization.

After approximately 24 hours the next step in preparing the liner material is to heat the composition to a temperature of 160°F. for about 15 minutes and at the same time to stir it violently until it attains homogeneous polymerization. At this point the liner material is "semi-cured".

In using the expression "semi-cured" in this application I wish to point out that the admixture can be cured by the application of heat at a temperature of 160°F. for about 5 minutes to produce a very soft material. It also can be cured by heating for about 15 minutes to produce a somewhat harder material. Completely cured material requires heat of boiling water at a maximum temperature of 212°F. Both the soft material and the somewhat harder material in the semi-cured state are capable of being completely cured by the further application of heat not exceeding the temperature of boiling water, for a somewhat longer period of time. Hence I refer to the material which has been semi-cured at a temperature of 160°F. for 5 minutes as a soft semi-cured material and I refer to the material which has been cured at 160°F. for about 15 minutes as a semi-cured harder material. It is to be understood that both of these materials are subject to final curing to finally set the same.

The soft semi-cured material is tacky and is somewhat rubber-like and readily conforms to irregular objects. Hence, it can be easily manually shaped to conform to irregular objects. In fact, the soft semi-cured material will flow from its own weight because it has no inherent rigidity. Thus in the use of the soft semi-cured material in dental practice this material preferably would be packaged in individual plastic bags of a triangular shape of about ¼ inch thick, 1½ inches wide and 2 inches long, for purposes which will now be stated.

The soft semi-cured material particularly lends itself to what is known in the dental art as "chairside application". By this I mean that a dentist having a patient in the dental chair whose denture requires lining material to compensate for gum recession, etc., as outlined above, can apply the soft semi-cured material to the denture by manual manipulation and then by the patient's normal bite have such soft semi-cured material forced outwardly to the sides of the denture from which it can be trimmed according to standard dental practice.

After the dentist has satisfied himself that the pre-existing acrylic denture to which he has applied the soft semi-cured lining material of the present invention has compensated for and filled in the gaps between the pre-existing denture and the jaw ridge, the denture with such soft semi-cured liner preferably is placed in water boiling at about 212°F. and kept there for an hour. At this temperature and during this period of time the soft semi-cured material cures itself sufficiently and serves as a soft liner for the denture and also gives proper adhesion to the denture and retention on the gums.

The semi-cured harder material is intended primarily for dental laboratory use to be applied to a newly made acrylic denture. The end result is that it will provide a soft liner about 1/16 inch thick over the entire denture surface which contacts the mouth tissue.

According to the present invention in preparing a new denture in a dental laboratory which will include a soft liner, the preferred steps to be followed are: to provide the dental flask or mold with a shim preferably of lead or wax in sheet form about 1/16 inch thick in contact with those surfaces of the flask or mold which ultimately will represent those surfaces which will contact the patient's mouth tissue. It probably should be mentioned that in dental practice that the flask or mold is comprised of two mold sections of which one half is shaped like a denture and the other half embodies the model which represents the patient's jaw. The two combined give rise to the final shape of the denture resulting from the molding operation.

With the shim in place in the flask the basic acrylic denture is molded under pressure and the acrylic with the shim is shaped to the cavity of the mold. The model half of the flask which conforms to the gum and mouth tissue is then removed to expose the shim and the shim is then also removed. The acrylic material which remains in the other half of the flask is then semi-cured by exposure to infra-red light until it becomes rigid enough so as not to be distorted by the pressure which will take place during application of the liner material.

It is then recommended that the semi-cured harder liner material provided by the present invention be cut up into small pieces and warmed up so as to facilitate its manipulation. These small pieces are placed in the previously prepared denture throughout the area where the shim had been disposed and the entire combination of semi-cured acrylic denture with the semi-cured harder liner material is placed back in the flask and subjected to heat and pressure to mold the same into a unitary structure which results in an acrylic denture having a soft liner completely adhered thereto.

The lining material as thus provided by the present invention has the advantage that it will yield under any indentation force and will gradually restore itself when such indentation force is removed. This characteristic of the material gives rise to the fact that when indented it does not apply pressure on the high points of the jaw ridge which caused the indentation. Also, in its finally-cured state there is an acrylic to acrylic connection between the liner and the denture which results from the natural process of curing. It will thus be understood that the monomer serves the dual purpose of initially dissolving the polymer to make the paste material and secondly in final curing of the denture with the liner material the monomer combines with the polymer of the denture to cause a cohesive structure.

With other liners such as silicon rubber, which has heretofore been used, the liner had to be cemented to the acrylic in order to adhere it to the same. The use of a cement was not always successful, and separations would take place between the silicon rubber liner and the acrylic denture.

What I claim is:

1. A liner material for polymerized methylmethacrylate denture restorations consisting essentially of an admixture of approximately 40% of finely powdered methylmethacrylate polymer, approximately 10% of methylmethacrylate monomer, and approximately 50% of butyl phthalyl butyl glycolate, which has been semi-cured for approximately 15 minutes at a temperature of about 160°F. into a somewhat hard material, capable of being softened by application of heat and pressure and finally cured at approximately 212°F. with a denture to adhere thereto and to provide a soft liner therefor.

2. The method of preparing a liner material for polymerized methylmethacrylate denture restorations comprising the steps of:
   a. admixing approximately 40% by weight of methylmethacrylate polymer, 10% by weight of methylmethacrylate monomer and approximately 50% by weight of butyl phthalyl butyl glycolate,
   b. permitting said mixture to stand without heating for approximately 24 hours until the same is thoroughly plasticized,
   c. heating the mixture at a temperature of approximately 160°F. for about 5 minutes and at the same time actively stirring the same until it attains homogeneous polymerization, whereby the material is semi-cured into a soft, tacky material having no inherent rigidity, which is capable of being manually shaped to conform to irregular objects.

3. The method of preparing a liner material for polymerized methylmethacrylate denture restorations comprising the steps of:
   a. admixing approximately 40% by weight of methylmethacrylate polymer, 10% by weight of methylmethacrylate monomer and approximately 50% by weight of butyl phthalyl butyl glycolate,
   b. permitting said mixture to stand without heating for approximately 24 hours until the same is thoroughly plasticized,
   c. heating the mixture at a temperature of approximately 160°F. for about 15 minutes and at the same time actively stirring the same until it attains homogeneous polymerization, whereby the material is semi-cured into a somewhat hard, tacky material having inherent rigidity, for later application to a denture.

* * * * *